US009386772B2

(12) United States Patent
Krogman et al.

(10) Patent No.: US 9,386,772 B2
(45) Date of Patent: Jul. 12, 2016

(54) ANTIMICROBIAL ELASTOMERIC ARTICLES

(75) Inventors: Nicholas Krogman, Pleasant Prairie, WI (US); Walt Isaac, Lindenhurst, IL (US); Shiping Wang, Libertyville, IL (US); Katia Petrov, Vernon Hills, IL (US)

(73) Assignee: Allegiance Corporation, Waukegan, IL (US)

( * ) Notice: Subject to any disclaimer, the term of this patent is extended or adjusted under 35 U.S.C. 154(b) by 191 days.

(21) Appl. No.: 13/396,260

(22) Filed: Feb. 14, 2012

(65) Prior Publication Data

US 2013/0209536 A1 Aug. 15, 2013

(51) Int. Cl.
| | |
|---|---|
| *A61K 9/70* | (2006.01) |
| *A01N 47/44* | (2006.01) |
| *A61L 29/08* | (2006.01) |
| *A61L 29/16* | (2006.01) |
| *A61L 31/10* | (2006.01) |
| *A61L 31/16* | (2006.01) |
| *A61B 19/04* | (2006.01) |
| *A01N 25/10* | (2006.01) |
| *A01N 25/34* | (2006.01) |
| *A61B 17/00* | (2006.01) |

(52) U.S. Cl.
CPC ............... *A01N 47/44* (2013.01); *A01N 25/10* (2013.01); *A01N 25/34* (2013.01); *A61B 19/04* (2013.01); *A61L 29/085* (2013.01); *A61L 29/16* (2013.01); *A61L 31/10* (2013.01); *A61L 31/16* (2013.01); *A61B 2017/00889* (2013.01); *A61L 2300/404* (2013.01)

(58) Field of Classification Search
None
See application file for complete search history.

(56) References Cited

U.S. PATENT DOCUMENTS

| | | | |
|---|---|---|---|
| 4,135,622 A | 1/1979 | Glick | |
| 6,448,306 B1 | 9/2002 | Lever et al. | |
| 7,833,548 B2 * | 11/2010 | Chappa et al. | 424/486 |
| 2004/0126604 A1 | 7/2004 | Wang et al. | |
| 2004/0241201 A1 | 12/2004 | Wang et al. | |
| 2005/0186258 A1 * | 8/2005 | Wang et al. | 424/443 |
| 2006/0251839 A1 | 11/2006 | Wang et al. | |
| 2007/0104766 A1 * | 5/2007 | Wang et al. | 424/443 |
| 2011/0054417 A1 | 3/2011 | Chappa et al. | |

FOREIGN PATENT DOCUMENTS

| | | |
|---|---|---|
| CN | 1780876 A | 5/2006 |
| CN | 101163585 A | 4/2008 |
| CN | 101351163 A | 1/2009 |
| WO | WO-2005082142 A1 | 9/2005 |
| WO | WO-2007058880 A2 | 5/2007 |

OTHER PUBLICATIONS

Draft Guidance for Industry and FDA Staff, Premarket Notification [510(k)] Submissions for Medical Devices that Include Antimicrobial Agents. Issued on Jul. 19, 2007, 18 pages.
ASTM International. "Standard Specification for Nitrile Examination Gloves for Medical Application." ASTM Standard D6319-10, published Jun. 2010, 4 pages.
Klevens et al., "Estimating Health Care-Associated Infections and Deaths in U.S. Hospitals, 2002." Public Health Reports vol. 122 (Mar./Apr. 2007), pp. 160-166.
Young, Lee W. International Search Report & Written Opinion issued in Application No. PCT/US13/26161. Mailed Apr. 26, 2013, 10 pages.
ASTM International. "Standard Practice for Determination of Expiration Dating for Medical Gloves." ASTM Standard D7160-05, published Sep. 2010, 7 pages.
The State Intellectual Property Office of the People's Republic of China, First Office Action mailed in Chinese Patent Application No. 201380009196.4, mailed May 25, 2015, 41 pages.
Zhao Zhenkui, "Process and Practical Technique for Sintering Bricks and Tiles," China Building Materials Press, Jan. 2012, pp. 16-17.
Australian Examination Report for Application No. 2013221551, mailed on Jan. 8, 2016, 3 pages.
Extended European Search Report for Application No. EP13749587.5, mailed on Aug. 20, 2015, 6 pages.
New Zealand Examination Report for Application No. 629182, mailed on May 25, 2015, 2 pages.

* cited by examiner

*Primary Examiner* — Brian Gulledge
(74) *Attorney, Agent, or Firm* — Amanda F. Maharaj

(57) ABSTRACT

The present invention relates generally to methods of preparing antimicrobial elastomeric articles that include an elastomeric article having an antimicrobial coating provided thereon. The antimicrobial elastomeric articles exhibit enhanced ability to reduce or eliminate microbes that come in contact with the article. Certain aspects of the invention are further directed to methods of packaging the antimicrobial elastomeric articles, where the packaged antimicrobial articles exhibit antimicrobial effectiveness for an extended period of time as compared to unpackaged antimicrobial articles. Antimicrobial elastomeric articles and packaged antimicrobial elastomeric articles prepared in accordance with the methods of the present invention are also provided.

31 Claims, No Drawings

ANTIMICROBIAL ELASTOMERIC ARTICLES

BACKGROUND OF THE INVENTION

1. Field of the Invention

The present invention relates generally to methods of preparing antimicrobial elastomeric articles that include an elastomeric article having an antimicrobial coating provided thereon. The antimicrobial elastomeric articles exhibit enhanced ability to reduce or eliminate microbes that come in contact with the article. Certain aspects of the invention are further directed to methods of packaging the antimicrobial elastomeric articles, where the packaged antimicrobial articles exhibit antimicrobial effectiveness for an extended period of time as compared to unpackaged antimicrobial articles. Antimicrobial elastomeric articles and packaged antimicrobial elastomeric articles prepared in accordance with the methods of the present invention are also provided.

2. Description of the Related Art

Gloves are used regularly in clinical and hospital environments by healthcare workers as personal protective equipment. While medical gloves are primarily used to protect the individual wearing the gloves, they also prevent transfer of microorganisms from the healthcare worker to the patient. However, cross contamination can still occur, especially if a healthcare worker contacts a non-sterile surface (e.g., a bedrail) while wearing a pair of gloves, and then contacts the patient without first changing into a new pair of gloves. This scenario can lead to the transfer of microorganisms from the non-sterile surface to a susceptible patient, which may result in an undesirable nosocomial (or "hospital-acquired") infection. Infections are considered nosocomial if they first appear 48 hours or more after hospital admission or within 30 days after discharge.

About 1.7 million patients get sick in hospitals each year from infections they acquired while in the hospital. Of those 1.7 million, approximately 100,000 die as a result of their infection. (Klevins et al., "Estimating Health Care-Associated Infections and Deaths in U.S. Hospitals, 2002," *Public Health Reports* Vol. 122 (March/April 2007)). In order to combat nosocomial infections, the CDC is promoting a campaign based on preventing infections, diagnosing and treating infections appropriately, using antibiotics wisely, and preventing transmission of microbes. Specific recommendations related to the prevention of infection transmission include having health care providers and personnel keep their hands clean at all times. However, in many hospitals there is poor adherence to hand hygiene guidelines. Healthcare workers face many obstacles in their attempt to keep clean hands. They might not be able to find a sink or a replacement pair of gloves, they have limited time between patients, and after washing their hands as many as 30 times during a work shift they may have serious problems with skin irritation and dryness.

In view of the ongoing need to minimize the risk of nosocomial infections, several approaches have been developed.

U.S. Published Patent Application No. US 2005/0186258 describes elastomeric articles coated by antimicrobial compositions and protected by water-resistant packaging. The antimicrobial gloves are useful in methods for reducing nosocomial infection by Gram positive bacteria, Gram negative bacteria, fungi, and viruses. The antimicrobial gloves may be packaged to maintain quick-kill activity against microbes, even after extended storage. The packaging protects the antimicrobial activity of a glove during storage and transportation by shielding the glove from warm and/or humid environments.

U.S. Published Patent Application No. US 2007/0104766 describes a surface treatment for elastomeric articles such as medical gloves coated with a water-based coating formulation having antimicrobial agent(s) therein. The coating includes a controlled-release matrix having a blend of a hydrophilic polymer and a hydrophobic component.

There is a need in the art for antimicrobial elastomeric articles that are useful for reducing the occurrence of nosocomial infections, for example, by providing a quick kill of microorganisms that contact the article.

SUMMARY OF THE INVENTION

The present invention meets the unmet needs of the art, as well as others, by providing methods for preparing antimicrobial elastomeric articles that exhibit enhanced ability to reduce or eliminate microbes that come in contact with the article. Also provided are methods of packaging the antimicrobial elastomeric articles to provide extended effectiveness for the antimicrobial agent.

According to one aspect of the invention a method for preparing an antimicrobial elastomeric article is provided that includes exposing an elastomeric article to an environment comprising about 10.3 $g/m^3$ or less absolute humidity; coating the elastomeric article with an antimicrobial coating composition to form an antimicrobial elastomeric article; and exposing the antimicrobial elastomeric article to an environment comprising about 10.3 $g/m^3$ or less absolute humidity. Preferably, the antimicrobial elastomeric article reduces the initial number of microorganisms present on a surface by at least 4 $\log_{10}$ within 5 minutes of being contacted by the antimicrobial elastomeric article.

An additional aspect of the invention relates to an antimicrobial elastomeric article prepared in accordance with the methods of the invention.

Another additional aspect of the invention relates to an antimicrobial elastomeric article prepared in accordance with the methods of the invention that is provided in a packaging system that permits the antimicrobial elastomeric article to reduce the initial number of microorganisms present on a surface by at least 4 $\log_{10}$ within 5 minutes of being contacted by the antimicrobial elastomeric article, for at least 12 weeks following packaging.

Another aspect of the invention relates to a method for preparing an antimicrobial elastomeric article that includes exposing the elastomeric article to an environment comprising about 10.3 $g/m^3$ or less absolute humidity, and coating the elastomeric article with an antimicrobial coating composition to form an antimicrobial elastomeric article. Preferably, the antimicrobial elastomeric article reduces the number of microorganisms present on a surface by at least 4 $\log_{10}$ within 5 minutes of being contacted by the antimicrobial elastomeric article.

According to a further aspect, the invention relates to a method for preparing an antimicrobial elastomeric article that includes coating the elastomeric article with an antimicrobial coating composition to form an antimicrobial elastomeric article, and exposing the antimicrobial elastomeric article to an environment comprising about 10.3 $g/m^3$ or less absolute humidity. Preferably, the antimicrobial elastomeric article reduces the number of microorganisms present on a surface by at least 4 $\log_{10}$ within 5 minutes of being contacted by the antimicrobial elastomeric article.

Other novel features and advantages of the present invention will become apparent to those skilled in the art upon examination of the following or upon learning by practice of the invention.

DETAILED DESCRIPTION OF THE INVENTION

The present invention relates generally to methods of preparing antimicrobial elastomeric articles that include an elastomeric article having an antimicrobial coating provided thereon. The antimicrobial elastomeric articles prepared using the methods exhibit enhanced ability to reduce or eliminate microbes that come in contact with the articles. Certain aspects of the invention are further directed to methods of packaging the antimicrobial elastomeric articles, where the packaged antimicrobial articles exhibit antimicrobial effectiveness for an extended period of time as compared to unpackaged antimicrobial articles. Antimicrobial elastomeric articles and packaged antimicrobial elastomeric articles prepared in accordance with the methods of the present invention are also provided.

The present invention was designed to mitigate the risk of cross contamination of microorganisms, particularly when used in a medical environment, although use in other environments, including laboratories and cleanroom facilities, is also envisioned. The antimicrobial elastomeric articles preferably exhibit quick-kill ability when contacted by a contaminated surface. "Quick-kill" refers to the ability to reduce the number of microorganisms present on a surface within 5 minutes of contact by a 4 $\log_{10}$ reduction or greater, preferably a 4.2 $\log_{10}$ reduction or greater, and more preferably a 4.5 $\log_{10}$ reduction or greater. According to some aspects, the reduction in microorganisms is also evaluated following accelerated aging carried out in accordance with ASTM D 6319-00a$^{\epsilon 3}$, Test Method D 573. Preferably, the antimicrobial coating maintains this level of antimicrobial efficacy throughout the lifetime of the product, such as at least 6 months, preferably at least one year, more preferably at least two years, and most preferably at least three years, which includes transportation and storage shelf-life.

However, maintaining the antimicrobial efficacy over extended periods presents a challenge. In prior applications, the antimicrobial agent tended to migrate from the outer surface of the elastomeric article into the body of the article over time, causing a decrease in efficacy. The present invention relates to new methods for preparing antimicrobial elastomeric articles, and methods for packaging the antimicrobial elastomeric articles to maintain quick-kill ability. Without wishing to be bound by theory, this migration was most likely facilitated by exposure of the antimicrobial elastomeric article to moisture, which acts as a vehicle for the diffusion of the antimicrobial agent into the body of the elastomeric article. This migration leads to decreased antimicrobial efficacy at the time of use. Reduction in antimicrobial efficacy may alleviated by the use of the inventive coating and packaging methods, resulting in the inventive antimicrobial elastomeric articles.

The antimicrobial coating compositions, antimicrobial elastomeric articles, and packaging for antimicrobial elastomeric articles are described in greater detail below.

Antimicrobial Coating

The antimicrobial elastomeric articles are coated with an antimicrobial coating, where the antimicrobial coating provides antimicrobial efficacy to the elastomeric article. Preferably, the antimicrobial coating includes one or more antimicrobial agents in a controlled-release matrix, where the matrix may include a blend of at least one hydrophilic polymer and at least one hydrophobic oligomer. The antimicrobial coating composition may be beneficially formulated as a water-based antimicrobial coating composition in order to avoid issues that arise when handling solvents, although elastomer-compatible, solvent-based formulations are also envisioned.

The antimicrobial elastomeric articles are capable of killing or restricting the growth of one or more of the following microbes: coagulase-negative Staphylococci, Enterococci, fungi, Candida albicans, Staphylococcus aureus, Enterobacter species, Enterococcus faecalis, Staphylococcus epidermidis, Streptococcus viridans, Escherichia coli, Klebsiella pneumoniae, Proteus mirabilis, Pseudomonas aeruginosa, Acinetobacter baumannii, Burkholderia cepacia, Varicella, Clostridium difficile, Clostridium sordellii, Hepatitis A, Hepatitis B, Hepatitis C, HIV/AIDS, methicillin-resistant Staphylococcus aureus (MRSA), mumps, norovirus, parvovirus, poliovirus, rubella, SARS, S. pneumoniae (including drug resistant forms), vancomycin-intermediate Staphylococcus aureus (VISA), vancomycin-resistant Staphylococcus aureus (VRSA), and vancomycin-resistant Enterococci (VRE). Preferably, the antimicrobial elastomeric articles have "quick-kill" capabilities against a broad spectrum of microorganisms. "Quick-kill" refers to the ability to reduce the number of microorganisms present on a surface within 5 minutes of contact by a 4 $\log_{10}$ reduction or greater, preferably a 4.2 $\log_{10}$ reduction or greater, and more preferably a 4.5 $\log_{10}$ reduction or greater.

Antimicrobial agents that may be used in the antimicrobial coating may include any agent capable of killing or inhibiting the growth of bacteria, fungi, viruses and/or parasites. For example, suitable antimicrobial agents include, without limitation, one or more of the following agents: biguanides (e.g., chlorhexidine digluconate (CHG), chlorhexidine diacetate, chlorhexidine dihydrochloride, chlorhexidine diphosphanilate, poly(hexamethylene biguanide) (PHMB)), rifampin, minocycline, silver compounds (silver chloride, silver oxide, silver sulfadiazine), triclosan, quaternary ammonium compounds (e.g., benzalkonium chloride, tridodecyl methyl ammonium chloride, didecyl dimethyl ammonium chloride, chloroallyl hexaminium chloride, benzethonium chloride, methylbenzethonium chloride, cetyl trimethyl ammonium bromide, cetyl pyridinium chloride, dioctyldimethyl ammonium chloride), iron-sequestering glycoproteins (e.g., lactoferrin, ovotransferrin/conalbumin), cationic polypeptides (e.g., protamine, polylysine, lysozyme), surfactants (e.g., SDS, Tween-80, surfactin, Nonoxynol-9) and zinc pyrithione. Further preferred antimicrobial agents include broad-spectrum antibiotics (quinolones, fluoroquinolones, aminoglycosides and sulfonamides), and antiseptic agents (iodine, methenamine, nitrofurantoin, validixic acid). The preferred antimicrobial agents for a quick-kill application are chlorhexidine digluconate (CHG), chlorhexidine diacetate, chlorhexidine dihydrochloride, chlorhexidine diphosphanilate, and poly(hexamethylene biguanide) (PHMB). It is considered to be within the ability of one skilled in the art to determine the type of antimicrobial agent and amount necessary to achieve adequate levels of antimicrobial activity against target microbes. Preferably, the antimicrobial agent covers at least 85% of the outside surface of the elastomeric article, more preferably 90%, even more preferably 95%, and most preferably covers at least 99.8% of the outside surface area of the elastomeric article.

The antimicrobial agent can be present in an amount ranging from 0.5% to 85% by weight of total solids of the antimicrobial coating composition, more preferably from 1.0% to 75% by weight of total solids, and most preferably from 2.5% to 60% by weight of total solids. Chlorhexidine is the most preferred antimicrobial agent. The minimum concentration of chlorhexidine at the surface of the elastomeric article is preferably greater than 7.6 µg/cm$^2$ in order to provide a 4-log efficacy against a broad spectrum of microbes.

The term "hydrophilic polymer" is used describe polymers or copolymers that are water soluble or water-dispersible; anionic, cationic, or nonionic; and crosslinked or non-crosslinked. Hydrophilic polymers usually include functional groups such as hydroxyl, amine, amide, ether, and other functional groups with a high affinity for water. Examples of hydrophilic polymers include, but are not limited to, polyvinyl alcohol, polyesters, polyacrylates, polyethers such as polyethylene glycol and polypropylene glycol, and cellulose and cellulose derivatives, such as carboxymethyl cellulose, hydroxyethyl cellulose, hydroxy ethyl methyl cellulose, and hydroxy propyl methyl cellulose. The hydrophilic polymer should also have good film-forming, binding, and adhesive properties. The preferred hydrophilic polymers are acrylic-based copolymers that include cationic dimethyl aminoalkyl units. This offers better water permeability to the resulting films. The preferred hydrophilic polymer is a copolymer of ethyl acrylate, methyl methacrylate and a low content of methacrylic acid ester with quaternary ammonium groups, sold as Eudragit® RS 30D by Evonik Inc. The hydrophilic polymer is present in amounts ranging from 0.5% to 99% by weight of total solids, more preferably present in an amount ranging from 1.0% to 75%, and most preferably ranging from 2.0% to 60% by weight of total solids.

The term "hydrophobic oligomer" is used to describe low to medium molecular weight polymers or copolymers that offer water resistance and aid in the film forming capabilities of the hydrophilic polymer. Examples of hydrophobic oligomers include, but are not limited to, fluorinated oligomers, chlorinated oligomers, short chain alkanes, silicones, and paraffin waxes. The hydrophobic oligomer is preferably dispersible in water; therefore paraffin wax is a preferred hydrophobic oligomer. The paraffin wax is a saturated hydrocarbon derived from petroleum with a chain length of 25-30 carbons. Non-ionic paraffin dispersions are preferred, such as Michem® Lube 743 (ML 743), sold by Michelman Inc. The hydrophobic oligomer can be present in amounts ranging from 0.5% to 99% by weight of total solids, more preferably present in an amount ranging from 1.0% to 55%, and most preferably 1.5% to 40% by weight of total solids.

Additional ingredients, such as wetting agents and antifoaming agents, may also be added to the formulation to ensure that the antimicrobial properties are optimized. A wetting agent is described as an agent that improves the coating film quality by allowing for quick spreading and uniform coverage. Wetting agents are well known in that art. The preferred wetting agents include a nonionic polyether dimethylpolysiloxane dispersion, sold as BYK 348 by BYK Chemie. Antifoaming agents are added to improve the dried coating quality. The preferred antifoaming agent is ethylene glycol-based, such as Surfynol® TG by Air Products.

Antimicrobial Elastomeric Articles

Articles according to the invention comprise an elastomeric article having a coating with sustainable antimicrobial activity.

The antimicrobial elastomeric articles of the present invention are preferably provided in the form of gloves, specifically medical gloves, and more specifically examination and surgical gloves. However, it is considered within the ability of those skilled in the art to prepare alternative antimicrobial elastomeric articles other than gloves, including, but not limited to, condoms, probe covers, dental dams, finger cots, catheters, and the like, using the guidance provided herein.

According to some aspects of the invention, elastomeric articles are provided that include multiple elastomeric layers, where the multiple elastomeric layers may have the same or different compositions. Preferred elastomers include, without limitation, natural rubber, polyurethane, polybutadiene, polychloroprene (Neoprene), nitrile rubber, block copolymers of styrene and butadiene, block copolymers of styrene and isoprene, and polyisoprene.

According to further aspects of the invention, the elastomeric articles may be formed either with, or without, powder. Although powder is a commonly-used donning agent, it is also associated with allergic reactions, and therefore another aspect of the invention relates to powder-free or substantially powder-free antimicrobial elastomeric articles prepared in accordance with the methods described above.

Pre-formed elastomeric articles prepared using conventional techniques may be prepared for coating with the antimicrobial coating formulation by storing the gloves in a controlled environment that is desiccated or dehumidified prior to applying the coating. The temperature of the environment may range from about 10° C. to about 30° C., preferably from about 17° C. to about 27° C., and is most preferably about 23° C. The relative humidity of the environment may range from about 0% relative humidity to about 55% relative humidity, preferably from about 15% relative humidity to about 50% relative humidity, and is most preferably from about 30% relative humidity to about 45% relative humidity. For example, an atmosphere of about 50% relative humidity or less at 23° C. may be used to prepare the elastomeric articles for the coating process. Ultimately, and most preferably, the environment in which the elastomeric articles are treated should have an absolute humidity of from about 0 g/m$^3$ to about 10.3 g/m$^3$ or less, regardless of the temperature, preferably from about 1.5 g/m$^3$ to about 9.8 g/m$^3$, more preferably from about 3.0 g/m$^3$ to about 9.3 g/m$^3$, and most preferably from about 4.5 g/m$^3$ to about 8.8 g/m$^3$. By knowing the desired absolute humidity, one skilled in the art is able to approximate the temperature and relative humidity levels at a given atmospheric pressure that would be suitable to maintain that absolute humidity in a controlled environment. The elastomeric articles may be treated in the desiccated/dehumidified controlled environment for a period of from about 12 to about 48 hours, preferably from about 18 to about 36 hours, and more preferably about 24 hours. It should be noted that controlled temperature and humidity may be provided in the vicinity of the articles by a variety of methods. These may include, but are not limited to, placing the articles in controlled-atmosphere rooms, sealed packages or bags with or without desiccants provided therein, closed boxes or totes with or without desiccants provided therein, or other means for providing an enclosed space capable of maintaining a desired level of temperature and humidity. Preferred desiccants may be selected from the group consisting of silica gel, aerogel, bentonite clay, activated alumina, nitrogen gas, and argon gas.

The antimicrobial coating composition may be applied to the elastomeric articles using conventional equipment and techniques readily available to those in the field of manufacturing elastomeric articles, including on-line and off-line techniques such as dipping, spraying, tumbling and the like. Examples of coating techniques are described in U.S. Pat. Pub. No. 2004/0126604 and U.S. Pat. Pub. No. 2004/0241201. For preparing surgical gloves, a preferred method of application is off-line spraying. For the preparation of examination gloves, a preferred on-line method of application is dip coating, and a preferred off-line method is the tumbling method of coating. Regardless of the particular application technique selected, the coating is preferably applied while the elastomeric articles are heated to 55° C.±5° C., and the coated elastomeric article is preferably dried at 55° C.±5° C. for about 30 minutes. The coating may be applied to the outer surface of the elastomeric article, the inner surface of the elastomeric article, or both the inner and outer surface of the elastomeric article. In the context of elastomeric articles such as gloves, the "outer" surface is the surface that comes into contact with the environment, while the "inner" surface is the surface that is primarily in contact with the user wearing the glove.

After the elastomeric articles have been coated with the antimicrobial composition and dried, the elastomeric articles may be subjected to a follow-up treatment in a controlled environment that is desiccated or dehumidified. The temperature of the environment may range from about 10° C. to about 30° C., preferably from about 17° C. to about 27° C., and is most preferably about 23° C. The relative humidity of the environment may range from about 0% relative humidity to about 55% relative humidity, preferably from about 15% relative humidity to about 50% relative humidity, and is most preferably from about 30% relative humidity to about 45% relative humidity. For example, an atmosphere of about 50% relative humidity or less at 23° C. may be used to conduct the follow-up treatment process. Ultimately, and most preferably, the environment in which the elastomeric articles are treated should have an absolute humidity of from about 0 g/m$^3$ to about 10.3 g/m$^3$ or less, regardless of the temperature, preferably from about 1.5 g/m$^3$ to about 9.8 g/m$^3$, more preferably from about 3.0 g/m$^3$ to about 9.3 g/m$^3$, and most preferably from about 4.5 g/m$^3$ to about 8.8 g/m$^3$. By knowing the desired absolute humidity, one skilled in the art is able to approximate the temperature and relative humidity levels at a given atmospheric pressure that would be suitable to maintain that absolute humidity in a controlled environment. The elastomeric articles may be treated in the desiccated/dehumidified controlled environment for a period of from about 12 to about 48 hours, preferably from about 18 to about 36 hours, and more preferably about 24 hours. It should be noted that controlled temperature and humidity may be provided in the vicinity of the articles by a variety of methods. These may include, but are not limited to, placing the articles in controlled-atmosphere rooms, sealed packages or bags with or without desiccants provided therein, closed totes with or without desiccants provided therein, or other means for providing an enclosed space capable of maintaining a desired level of temperature and humidity.

According to some aspects of the invention, the elastomeric articles may be subjected to either pre-treatment or post-treatment processing in a desiccated environment, as described above, or the elastomeric articles may be subjected to both pre-treatment and post-treatment processing. Without wishing to be limited by theory, it is believed that the desiccating treatment steps are useful for maintaining quick-kill efficacy of the antimicrobial elastomeric article following storage. Antimicrobial elastomeric articles prepared in accordance with the processing methods described above beneficially maintain an unexpectedly high level of antimicrobial efficacy as compared to elastomeric articles provided with antimicrobial coatings that are applied using prior techniques.

Following the process of coating the elastomeric article with the antimicrobial coating composition, the elastomeric articles may be stored in a desiccated environment until they can be packaged, or they may directly proceed to the packaging step.

Packaging of Antimicrobial Elastomeric Articles

The present invention provides elastomeric articles having an antimicrobial coating thereon, where the antimicrobial elastomeric articles exhibit quick-kill antimicrobial efficacy. In order to maintain the efficacy of the antimicrobial elastomeric articles following storage and transportation, the elastomeric articles may be packaged. The packaging preferably maintains a low level of humidity in the environment surrounding the antimicrobial elastomeric article.

Any packaging material and/or technique that is capable of providing a low vapor-permeable package may be used in accordance with the present invention. Suitable materials that may be useful for packaging elastomeric articles include, but are not limited to, aluminum foil (or foils formed from other metals/alloys), polyethylene, and nylon-based multi-layer films, as well as laminates containing different film layers, such as aluminum/nylon laminates. One preferred package design consists of aluminum foil that contains the internal atmosphere of the packaging, with the elastomeric articles inside, via a hermetic seal. According to some aspects, the packaging material provides a 100% barrier against transmission of humidity into the package (i.e., 0% water vapor transmission).

Regardless of the type of elastomeric article or the specific packaging technique, before the outer package is sealed, preferably as much humidity- or moisture-containing air as possible is removed from the package to provide a reduced-humidity environment for the elastomeric article provided within the package, as compared to the environment outside the package. This may be done by using one or more of the following techniques:

(a) Removing humidity- or moisture-containing air from an enclosed compartment (or chamber) in which an elastomeric article, which may optionally be wrapped in an inner packet, is placed. The elastomeric article may be sandwiched between a top web film and a bottom web film (which may be provided, for example, in the form of a shallow tray) before sealing the film with heat and pressure to form the outer package. Air may be sucked out from the enclosed compartment (or chamber) by connecting it to a vacuum pump or other apparatus before sealing the outer package. This method of packaging is referred to as thermo "form fill seal" packaging.

(b) Mechanically squeezing out humidity- or moisture-containing air from the unsealed package including the elastomeric article, which optionally may be wrapped in an inner packet. The elastomeric article then may be sandwiched between a top web film and a bottom web film to form the unsealed package before sealing the package with heat and/or pressure. This method of packaging is referred to as "platen seal" packaging.

(c) Flushing air out of the unsealed package with an inert gas, such as nitrogen, before sealing the package. This may be done using a "form fill seal" packaging machine where inert gas is used instead of applying a vacuum to remove the humidity- or moisture-containing air.

Any packaging material and/or technique that is capable of maintaining a reduced-humidity environment within the package may be used in accordance with the present invention.

The package containing the antimicrobial elastomeric article may also optionally include a desiccant material, particularly when the packaging material does not provide a 100% barrier against transmission of humidity. Desiccants that may be incorporated into the packaging used in the present invention may include, but are not limited to, silica gel, aerogel, bentonite clay, activated alumina, nitrogen gas, and argon gas. The dessicant may also be provided in the form of a vacuum-evacuated atmosphere within the package. One skilled in the art can also develop other means to control the atmosphere inside the packaging by either evacuating the inside of the packaging or to fill the packaging with an inert atmosphere such as nitrogen or argon.

Without wishing to be bound by theory, it is believed that a low vapor-permeable package maintains the high level of antimicrobial efficacy of the antimicrobial elastomeric articles formed using the methods described above by minimizing the presence of water vapor in the environment surrounding the article. It is believed that the antimicrobial agent has a tendency to be absorbed into the body of the elastomeric article when in the presence of water. By limiting the amount of water vapor, less antimicrobial agent is absorbed into the elastomeric article, leaving more of the antimicrobial agent available at the surface of the article for the desired "quick-kill" ability at the surface of the elastomeric article. Preferably, the relative humidity inside the packaging system is below about 50% relative humidity. According to some aspects of the invention, even lower relative humidity may be maintained inside the package, such as less than about 40%, preferably less than about 30%, and more preferably less than about 10% or 5% relative humidity.

According to further aspects, the antimicrobial elastomeric articles that are packaged at ambient temperatures and up to 50% relative humidity (RH) may maintain quick-kill antimicrobial efficacy for at least 4 weeks following opening the package and exposing the contents to atmospheric conditions, preferably for at least 6 weeks, and more preferably for at least 8 weeks following opening the package.

It will be appreciated that package materials, desiccant, and pouch designs used for antimicrobial elastomeric articles in accordance with the invention can vary. For example, the amount of desiccant used can depend on the number of gloves being packed in a particular package, the barrier level provided by the packaging materials, and the environmental conditions during packaging.

Using these conditions, a quick-kill improvement of 1-log reduction on a five-minute exposure time is achieved, a 2-log reduction on a five-minute exposure time is preferred, and at least a 2-log reduction after a one-minute exposure time is more preferred. Using these conditions, a quick-kill efficacy of 4-log reduction on a five-minute exposure time is most preferred.

These and other aspects of the invention are further described in the non-limiting Examples set forth below.

EXAMPLES

Example 1

Example 1 demonstrates that efficacy of an antimicrobial coating that utilizes CHG as the active antimicrobial component. The coating consists of hydrophilic polymer and hydrophobic oligomer that produce a film containing the active agent. A wetting agent and low foaming agent are also added to the formulation to provide good coating quality.

TABLE 1

| Formulation 1-1 | Concentration (%) | Dry % | Amount (g) |
|---|---|---|---|
| CHG (20%) | 7.50 | 3.75 | 840.00 |
| Wetting Composition (3%) | 0.10 | 0.0075 | 11.20 |
| Eudragit ® RS 30D (30%) | 4.00 | 3.00 | 448.00 |
| ML 743 (32%) | 3.13 | 2.50 | 350.00 |
| DI Water | — | — | 9550.80 |
| Total | 14.73 | | 11200 |

Wetting composition: A 3% solution was prepared by adding 10 g of Surfynol® TG and 5 g of BYK-348 to 485 g of deionized water (DI water). The mixture was stirred for 20 minutes to achieve the desired concentrations of 2% Surfynol® TG and 1% of BYK-348.

Formulation 1-1: 11.20 g of wetting composition was added to 9550.80 g of DI water. This solution is mixed for at least 10 minutes. 840.00 g of CHG, 448.00 g of Eudragit® RS 30D, and 350.00 g of ML 743 are added individually to the solution and in that respective order. After the addition of each component, the solution is mixed for at least 10 minutes before the next component is added. Upon complete addition, the solution is stirred for an additional 10 minutes.

Glove Treatment: The nitrile gloves were subjected to a pretreatment process that involved the storage of gloves in a sealed tote that maintained a desiccated environment surrounding the gloves, wherein the environmental temperature was 23° C. and the relative humidity was 50%. The relative humidity level was achieved by placing a dessicant in the tote. The gloves remained in the desiccated environment for at least 24 hours prior to coating application. Following the pretreatment of the gloves, the surface of the glove was treated with antimicrobial coating using a spray coating technique. The gloves were heated to 55° C. during the application process. Following the application of the coating, the coated gloves were dried at 55° C. for 30 minutes, then immediately placed into a desiccated environment for at least 24 hours.

Antimicrobial Activity: The antimicrobial activity of sample 1-1 was tested before and after aging against *E. coli* and MRSA with a 5 minute exposure time:

TABLE 2

| Sample 1-1 | E. Coli | MRSA |
|---|---|---|
| Fresh | >5.37 | >4.56 |
| After Aging (7 days @ 70° C.) | 4.72 | 4.77 |

The test results show that with a single antimicrobial agent, antimicrobial activities can be maintained above 4 log reduction of both gram positive and gram negative microbes after aging for 7 days at 70° C.

Example 2

Example 2 demonstrates the conditions needed to provide a stable antimicrobial coating on the surface of the nitrile glove. The coating composition and formulation fabrication remained the same as describe in Example 1. Sample 2-1 describes coated gloves that were stored in desiccated environments (described above in Example 1) before and after the application of the antimicrobial coating. Samples 2-2 and 2-3 represent coated gloves that were pre- and post-conditioned (using the technique described above in Example 1), respectively. Sample 2-4 describes coated gloves that were not desiccated before or after application of the antimicrobial coating. Samples 2-1 through 2-4 were tested before and after conditioning against *E. coli* and MRSA with a 5 minute exposure time.

TABLE 3

|  | *E. coli* | | MRSA | |
| --- | --- | --- | --- | --- |
| Sample ID | Fresh | Aged (70° C., 7 days) | Fresh | Aged (70° C., 7 days) |
| Sample 2-1 | 5.37 | 4.37 | 4.56 | 4.24 |
| Sample 2-2 | 4.54 | 4.01 | 4.24 | 4.00 |
| Sample 2-3 | 4.27 | 4.57 | 4.35 | 4.13 |
| Sample 2-4 | 4.59 | 1.24 | 5.42 | 2.00 |

The test results demonstrate the need for conditioning of the gloves before and/or after the gloves are treated with the antimicrobial coating. The antimicrobial efficacy is believed to be lost due to the phenomenon described in U.S. Publ. Appl. No. 2007/0104766. This describes that effect of moisture on the antimicrobial glove and how the antimicrobial agent will migrate from the surface of the glove that is facilitated by the presence of water in the nitrile glove and in the surrounding environment. The antimicrobial efficacy is not affected when the gloves are tested after being freshly coated. However, when sample 2-4 is exposed to accelerated aging conditions following ASTM D 6319-00a$^{e3}$, Test Method D 573, the antimicrobial efficacy decreases. Samples 2-1, 2-2, and 2-3 are able to maintain the antimicrobial efficacy because of the desiccated storage conditions pre- and/or post-coating.

Example 3

Example 3 demonstrates the stability of the antimicrobial glove against relative humidity levels at ambient temperatures. The coating composition, formulation fabrication, and coating application method remained the same as described in Example 1. Sample 3-1 describes antimicrobial-coated gloves that were exposed to 23° C. with a relative humidity of 45%. Sample 3-2 describes antimicrobial-coated gloves that were exposed to 23° C. with a relative humidity of 55%. Sample 3-3 describes antimicrobial-coated gloves that were exposed to 23° C. with a relative humidity of 75%. All samples were tested after one and two weeks exposure to the temperature and humidity levels. Antimicrobial efficacy was recorded against *E. coli* after a 5 minute exposure time.

TABLE 4

|  |  | *E. coli* Log Reduction | |
| --- | --- | --- | --- |
| Sample | Sample Condition | 1 Week | 2 week |
| Sample 3-1 | 23° C., 45% RH | 5.38 | 4.7 |
| Sample 3-2 | 23° C., 55% RH | 3.93 | 2.59 |
| Sample 3-3 | 23° C., 75% RH | 3.08 | 1.39 |

The test results shown in Table 4 demonstrate the effect of humidity on the antimicrobial coated glove. At ambient temperatures, the antimicrobial glove starts to lose efficacy when the relative humidity is approximately 55% or greater. While not wishing to be bound by theory, it is believed that this humidity level causes the migration of CHG into the glove substrate from the antimicrobial coating.

Example 4

Example 4 demonstrates the need for robust packaging to maintain the antimicrobial efficacy of the antimicrobial coated glove. The coating composition, formulation fabrication, and coating application method remained the same as described in Example 1. Antimicrobial gloves were packed into two packaging prototypes. The prototypes contained the antimicrobial coated gloves and the prototypes were subjected to outside conditions meant to simulated real world conditions experienced by medical glove products. Sample 4-1 is a control glove that was not packaged. Sample 4-2 is a packaging prototype comprised of Amcor aluminum foil laminate packaging containing antimicrobial-coated gloves and desiccant. Sample 4-3 is a packaging prototype made from the same material as described in Sample 4-2, but this sample contained only antimicrobial-coated gloves and no desiccant. The samples were tested against *E. coli* and MRSA after exposure to 45° C. and 85% relative humidity for up to 16 weeks.

TABLE 5

| | Time Points | | | | | | | | | | | |
| --- | --- | --- | --- | --- | --- | --- | --- | --- | --- | --- | --- | --- |
| | Week 2 | | Week 4 | | Week 6 | | Week 8 | | Week 12 | | Week 16 | |
| Sample | *E. Coli* LR | MRSA LR | *E. Coli* LR | MRSA LR | *E. Coli* LR | MRSA LR | *E. Coli* LR | MRSA LR | *E. Coli* LR | MRSA LR | *E. Coli* LR | MRSA LR |
| Sample 4-1 | 0 | 0 | — | — | — | — | — | — | — | — | — | — |
| Sample 4-2 | 4.47 | 5.20 | 4.47 | 4.42 | 4.49 | 4.93 | 4.57 | 4.70 | 4.64 | 4.50 | 4.57 | 4.42 |
| Sample 4-3 | 4.47 | 4.68 | 4.47 | 4.42 | 4.61 | 5.07 | 4.57 | 4.59 | 4.50 | 4.19 | 4.79 | 4.68 |

The results show that the antimicrobial efficacy is maintained above 4 log reduction against *E. coli* and MRSA after 5 minutes of exposure time when packaged into an aluminum foil pouch that is hermetically sealed. A control glove was analyzed under similar conditions without packaging protection. The control gloves lost antimicrobial efficacy during the exposure period.

Example 5

Example 5 demonstrates the open package stability of the antimicrobial-coated gloves after being packaged and exposed to conditions described in Example 4. The coating composition, formulation fabrication, and coating application method remained the same as described in Example 1.

The packaging of the gloves and subsequent exposure to 45° C. and 85% relative humidity were the same as described in Example 4. Sample 5-1 is a packaging prototype comprised of Amcor aluminum foil laminate packaging containing antimicrobial-coated gloves and desiccant. Sample 5-2 is a packaging prototype made from the same material as described in Sample 5-1, but this sample contained only antimicrobial-coated gloves and no desiccant. Following exposure to 45° C. and 85% relative humidity, the packages were opened and maintained at ambient room conditions. Each sample was tested against *E. coli* and MRSA to show the maintenance of 4 log reduction in microbes after 5 minutes exposure time under these conditions.

TABLE 6

| Sample | Open Pouch Efficacy-4 weeks | |
|---|---|---|
| | *E. coli* | MRSA |
| Sample 5-1 | 4.24 | 4.70 |
| Sample 5-2 | 4.00 | 4.51 |

The results demonstrate the open pouch stability of the antimicrobial-coated gloves at up to 4 weeks after the antimicrobial-coated gloves have been exposed to simulated transportation conditions. This is an important simulation of actual product exposure through the supply chain to show that the final user is receiving a glove that possesses the efficacy to kill a broad spectrum of microbes.

Example 6

Example 6 demonstrates the minimum concentration of CHG needed to achieve 4 log efficacy in 5 minutes exposure time on an antimicrobial-coated glove. The formulation fabrication and coating application were the same as described in Example 1. The concentration of the active component, CHG, was varied in the formulation. These formulations were then applied to the gloves and the concentration of CHG needed on the coated glove in order to achieve at least 4 log efficacy was measured. The concentration of CHG was measured using UV-Visible spectroscopy with the assistance of a sodium hypobromite indicator. CHG was extracted from the glove using water and the unknown concentration was calculated versus a predetermined standard curve. The antimicrobial efficacy after an exposure time of 5 minutes was determined against *E. coli* and MRSA.

TABLE 7

| CHG Concentration | Log Reduction | |
|---|---|---|
| ($\mu g/cm^2$) | *E. coli* | MRSA |
| 2.09 | 1.67 | 3.08 |
| 7.63 | 4.18 | 4.16 |
| 11.90 | 4.72 | 4.06 |

The data demonstrates that about 7.6 µg of CHG is needed to offer 4 log antimicrobial efficacy against a broad spectrum of microbes.

Example 7

Example 7 describes the determination of surface area coverage by the antimicrobial agent on a medical glove. This was determined using an indicator comprised of cetyl trimethylammonium bromide (CTAB), mixed with water. Sodium hypobromite was added to solution and kept at approximately 37° C. An antimicrobial glove that was fabricated as described in Example 1 was then dipped into the indicator solution. The areas on the glove where CHG was coated turned a dark red color and the areas on the glove that were not coated on the glove remained the same color as the glove. These uncoated areas were measured, totaled, and it was calculated that greater that 99% of the glove is coated with CHG.

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, in order to more fully describe the state of the art to which this invention pertains.

The invention is capable of considerable modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the detailed description provided above.

What is claimed:

1. A method for preparing an antimicrobial elastomeric article, comprising:
   exposing an elastomeric article to an environment comprising about 10.3 $g/m^3$ or less absolute humidity;
   coating the elastomeric article with an antimicrobial coating composition to form an antimicrobial elastomeric article;
   exposing the antimicrobial elastomeric article to an environment comprising about 10.3 $g/m^3$ or less absolute humidity; and
   packaging the antimicrobial elastomeric article in a packaging system that does not comprise a desiccant selected from the group consisting of silica gel, aerogel, bentonite clay, activated alumina, nitrogen gas, and argon gas;
   wherein the antimicrobial elastomeric article, when aged in the packaging system for 7 days at 70°C., has an antimicrobial efficacy such that the number of microorganisms present on a surface of the antimicrobial elastomeric article is reduced by at least 4 $\log_{10}$ within 5 minutes.

2. The method of claim 1, wherein the elastomeric article is exposed to the environment for a period of from about 12 to about 48 hours.

3. The method of claim 1, wherein the antimicrobial elastomeric article is exposed to the environment for a period of from about 12 to about 48 hours.

4. The method of claim 1, wherein the environment comprising about 10.3 $g/m^3$ or less absolute humidity is maintained by a structure selected from the group consisting of rooms, bags, packages, boxes, and totes.

5. The method of claim 4, wherein the structure further comprises a desiccant selected from the group consisting of silica gel, aerogel, bentonite clay, activated alumina, nitrogen gas, and argon gas.

6. The method of claim 1, wherein the antimicrobial coating composition comprises an antimicrobial agent, a hydrophilic polymer, and a hydrophobic oligomer.

7. The method of claim 6, wherein the antimicrobial agent is selected from the group consisting of biguanides, rifampin, minocycline, silver compounds, triclosan, quaternary ammonium compounds, iron-sequestering glycoproteins, cationic polypeptides, surfactants, zinc pyrithione, broad-spectrum antibiotics, antiseptic agents, and combinations thereof.

8. The method of claim 7, wherein the antimicrobial agent comprises chlorhexidine gluconate.

9. The method of claim 7, wherein the biguanides are selected from the group consisting of chlorhexidine digluconate (CHG), chlorhexidine diacetate, chlorhexidine dihydrochloride, chlorhexidine diphosphanilate, and poly(hexamethylene biguanide) (PHMB).

10. The method of claim 7, wherein the silver compounds are selected from the group consisting of silver chloride, silver oxide, and silver sulfadiazine.

11. The method of claim 7, wherein the quaternary ammonium compounds are selected from the group consisting of benzalkonium chloride, tridodecyl methyl ammonium chloride, didecyl dimethyl ammonium chloride, chloroallyl hexaminium chloride, benzethonium chloride, methylbenzethonium chloride, cetyl trimethyl ammonium bromide, cetyl pyridinium chloride, and dioctyldimethyl ammonium chloride.

12. The method of claim 7, wherein the iron-sequestering glycoproteins are selected from the group consisting of lactoferrin and ovotransferrin/conalbumin.

13. The method of claim 7, wherein the cationic polypeptides are selected from the group consisting of protamine, polylysine, and lysozyme.

14. The method of claim 7, wherein the surfactants are selected from the group consisting of SDS, Tween-80, surfactin, and Nonoxynol-9.

15. The method of claim 7, wherein the broad-spectrum antibiotics are selected from the group consisting of quinolones, fluoroquinolones, aminoglycosides and sulfonamides.

16. The method of claim 7, wherein the antiseptic agents are selected from the group consisting of iodine, methenamine, nitrofurantoin, and validixic acid.

17. The method of claim 6, wherein the hydrophilic polymer comprises cationic acrylic copolymer of acrylic acid and methacrylic ester with quaternary ammonium groups.

18. The method of claim 6, wherein the hydrophobic oligomer comprises a nonionic paraffin wax of 25-30 carbons in chain length.

19. The method of claim 1, wherein the antimicrobial coating composition is applied by a technique selected from the group consisting of dipping, spraying, and tumbling.

20. The method of claim 19, wherein the antimicrobial coating composition is applied while the elastomeric article is heated to about 55° C.

21. The method of claim 1, further comprising a step of drying the antimicrobial elastomeric article at 55°C. ±5°C. for about 30 minutes after coating the elastomeric article with the antimicrobial coating composition.

22. The method of claim 1, wherein the antimicrobial elastomeric article reduces the number of one or more microbes selected from the group consisting of coagulase-negative *Staphylococci*, *Enterococci*, fungi, *Candida albicans*, *Staphylococcus aureus*, *Enterobacter species*, *Enterococcus faecalis*, *Staphylococcus epidermidis*, *Streptococcus viridans*, *Escherichia coli*, *Klebsiella pneumoniae*, *Proteus mirabilis*, *Pseudomonas aeruginosa*, *Acinetobacter baumannii*, *Burkholderia cepacia*, Varicella, *Clostridium difficile*, *Clostridium sordellii*, Hepatitis A, Hepatitis B, Hepatitis C, HIV/AIDS, methicillin-resistant *Staphylococcus aureus* (MRSA), mumps, norovirus, parvovirus, poliovirus, rubella, SARS, *S. pneumoniae*, vancomycin-intermediate *Staphylococcus aureus* (VISA), vancomycin-resistant *Staphylococcus aureus* (VRSA), and vancomycin-resistant *Enterococci* (VRE).

23. The method of claim 22, wherein the *S. pneumoniae* is a drug-resistant form of *S. pneuominae*.

24. The method of claim 1, wherein the packaging system comprises a packaging material selected from the group consisting of aluminum foil, polyethylene film, nylon film, and laminates thereof.

25. The method of claim 1, wherein the relative humidity inside the packaging system is below about 50% relative humidity.

26. The method of claim 1, wherein the antimicrobial elastomeric article has an antimicrobial efficacy such that the number of microorganisms present on a surface of the antimicrobial elastomeric article is reduced by at least 4 $\log_{10}$ within 5 minutes for from about 8 to about 26 weeks following packaging.

27. The method of claim 26, wherein the antimicrobial elastomeric article has an antimicrobial efficacy such that the number of microorganisms present on a surface of the antimicrobial elastomeric article is reduced by at least 4 $\log_{10}$ within 5 minutes for at least 4 weeks following opening the packaging system to ambient atmospheric conditions.

28. The method of claim 1, wherein the elastomeric article is selected from the group consisting of gloves, condoms, probe covers, and catheters.

29. A method for preparing an antimicrobial elastomeric article, comprising:
 exposing an elastomeric article to an environment comprising about 10.3 g/m$^3$ or less absolute humidity;
 coating the elastomeric article with an antimicrobial coating composition to form an antimicrobial elastomeric article; and
 packaging the antimicrobial elastomeric article in a packaging system that does not comprise a desiccant selected from the group consisting of silica gel, aerogel, bentonite clay, activated alumina, nitrogen gas, and argon gas;
 wherein the antimicrobial elastomeric article, when aged in the packaging system for 7 days at 70°C., has an antimicrobial efficacy such that the number of microorganisms present on a surface of the antimicrobial elastomeric article is reduced by at least 4 $\log_{10}$ within 5 minutes.

30. A method for preparing an antimicrobial elastomeric article, comprising:
 coating an elastomeric article with an antimicrobial coating composition to form an antimicrobial elastomeric article;
 exposing the antimicrobial elastomeric article to an environment comprising about 10.3 g/m$^3$ or less absolute humidity; and
 packaging the antimicrobial elastomeric article in a packaging system that does not comprise a desiccant selected from the group consisting of silica gel, aerogel, bentonite clay, activated alumina, nitrogen gas, and argon gas;
 wherein the antimicrobial elastomeric article, when aged in the packaging system for 7 days at 70°C., has an antimicrobial efficacy such that the number of microorganisms present on a surface of the antimicrobial elastomeric article is reduced by at least 4 $\log_{10}$ within 5 minutes.

31. The method of claim 30, further comprising a step of exposing the elastomeric article to an environment comprising about 10.3 g/m$^3$ or less absolute humidity.

\* \* \* \* \*